Figure 1:
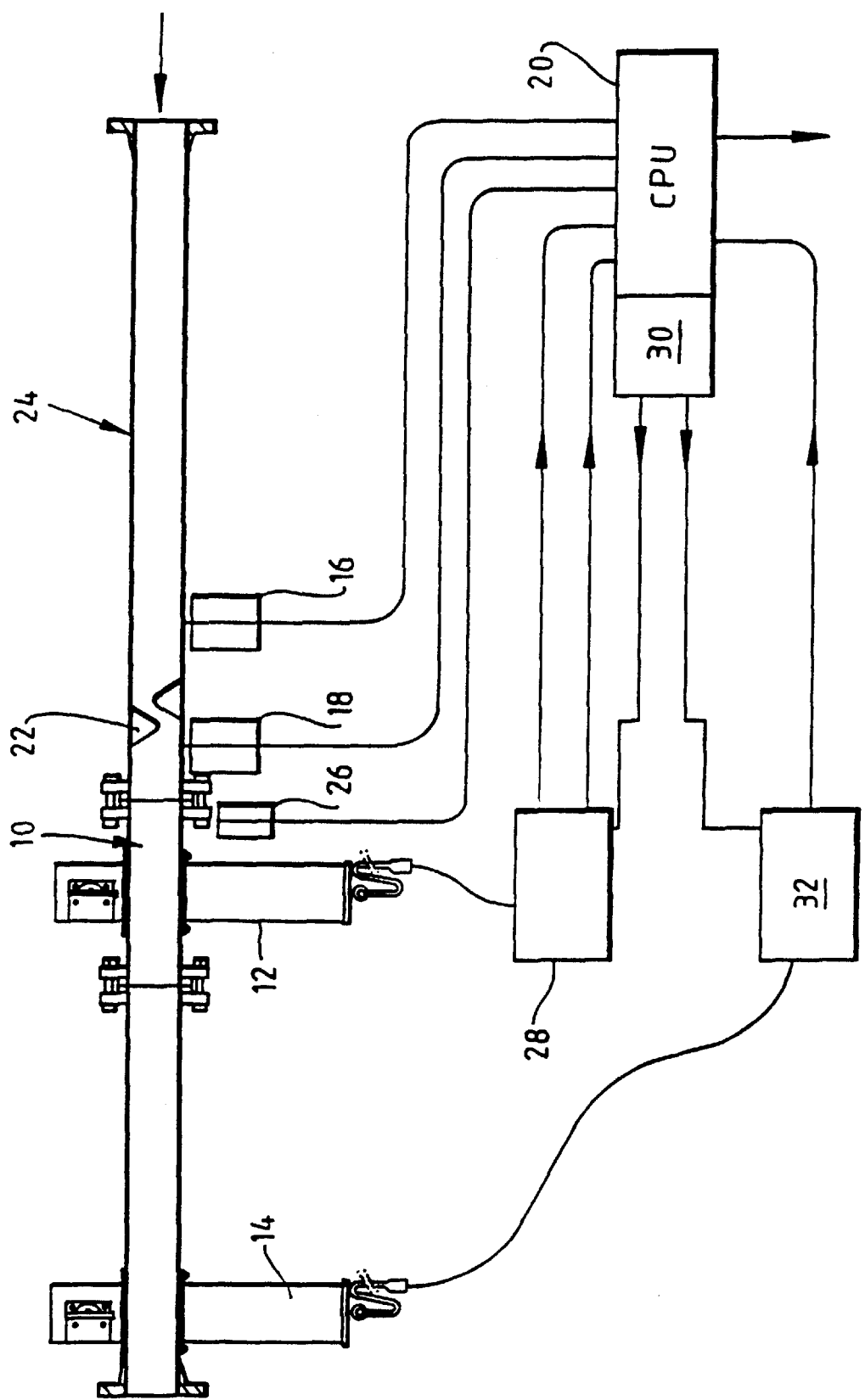

United States Patent
Hewitt et al.

[11] Patent Number: 5,822,390
[45] Date of Patent: Oct. 13, 1998

[54] APPARATUS FOR ANALYZING FLUID FLOW

[75] Inventors: Geoffrey Frederick Hewitt, Wallingford; George Lister Shires, Weymouth; Susan Joan Parry, Pirbright; Philip Antony Mark, Chester; Paul Stephen Harrison, Melverley, Nr. Oswestry, all of United Kingdom

[73] Assignee: I.C. Consultants Limited, London, United Kingdom

[21] Appl. No.: 809,696

[22] PCT Filed: Sep. 27, 1995

[86] PCT No.: PCT/GB95/02290

§ 371 Date: Jun. 10, 1997

§ 102(e) Date: Jun. 10, 1997

[87] PCT Pub. No.: WO96/10172

PCT Pub. Date: Apr. 4, 1996

[30] Foreign Application Priority Data

Sep. 28, 1994 [GB] United Kingdom ............... 9419510

[51] Int. Cl.⁶ .................................................. G01N 23/12
[52] U.S. Cl. ............................................. 378/53; 378/51
[58] Field of Search .............................. 378/53, 54, 57, 378/51; 250/356.1, 393, 394

[56] References Cited

U.S. PATENT DOCUMENTS 4,228,353  10/1980  Johnson ............................. 250/356.1
5,689,540  11/1997  Stephenson et al. ..................... 378/53

*Primary Examiner*—David P. Porta
*Attorney, Agent, or Firm*—Marshall & Melhorn

[57] ABSTRACT

The present invention is an apparatus for analyzing fluid flow in a pipe. The apparatus includes at least one radiation source to direct radiation through the flow and at least one radiation detector positioned to receive from the source or sources radiation which has passed through the flow. The radiation is emitted at least two different energies. Each detector provides a signal to a processing means. The processing means is arranged to process the signal to provide a series of chronological values. The chronological values are grouped by magnitude. The grouped chronological values are then analyzed by the analysis means.

18 Claims, 1 Drawing Sheet

APPARATUS FOR ANALYZING FLUID FLOW

The invention relates to a mixer and apparatus for analysing fluid flow.

One situation in which fluid flow analysis is important is in the production of oil from an oil well, or group of oil wells. Oil is commonly found mixed with water and gas thus providing a three phase fluid flow. Clearly, it is important to be able to determine how much of the fluid flow is constituted by each of the three phases.

Known apparatus for phase fraction analysis comprises two gamma radiation sources with associated detectors, which are spaced apart along a pipe in the flow direction. The sources emit radiation at different energies. The signals from the detectors are proportional to the gamma radiation received and hence indicate the radiation absorption from the flow. This information enables the phase fractions of the flow to be determined. The phase fractions of the flow may vary widely with time as the flow passes the detectors due the occurrence of slug flow, for example, and the analysis is consequently subject to inaccuracy, particularly as the relationship between radiation absorption and the amount of fluid intercepting the beam is exponential.

According to the invention there is provided apparatus for analysing fluid flow in a pipe comprising at least one radiation source to direct radiation through the flow, and at least one radiation detector positioned to receive from the source or sources radiation which has passed through the flow, the source or sources emitting radiation at least at two different energies, the or each detector providing a signal to processing means, the processing means being arranged to process the signal to provide a series of chronological values and to group the values by magnitude for analysis by analysis means.

As the signal becomes a series of values which are grouped, the analysis means can conduct a more sophisticated analysis than simple averaging and a more accurate analysis can be conducted. Preferably, the analysis means is arranged to determine the phase fractions in the flow. Alternatively, or in addition, the analysis means may be arranged to determine the type of flow e.g. slug flow or stratified flow. In addition the analysis of the signals by grouping provides information on the variation of composition of the mixture with time. For example in slug flow the oil/water ratios in the slug and in the thin film between slugs can be individually determined.

Preferably, radiation from the or each source will be measured over a series of short time intervals. In one embodiment, a single detector is provided. In that case, two sources may be provided, each emitting radiation at a different energy. In the prior system, necessary separation of the two sources lead to errors as the radiation beams did not "see" the same section of flow. Because of the processing and analysis which is carried out by the apparatus of the invention, this necessary separation is possible without incurring errors.

As an alternative to two sources, a single source can be used which is arranged to emit radiation of at least two different energies, e.g. a caesium source emitting radiation at 32 keV and 661 kev.

The apparatus is principally intended for use with three phase flow and so preferably radiation at only two different energies is emitted by the source or sources.

The radiation may be X-ray and/or gamma radiation.

The apparatus may include a mixer and means for sensing pressure drop across the mixer. This enables velocity calculations to be carried out when combined with means for sensing liquid hold-up. The sensing means are preferably associated with the analysis means which is arranged to determine flow rate. The means for sensing the liquid hold-up may comprise at least one radiation source to direct radiation through the flow to at least one radiation detector positioned to receive radiation which has passed through the flow from the or each source.

In one embodiment, the apparatus includes only two sources and only two detectors and the analysis means is arranged to determine both phase fraction and flow rate. Phase fraction is determined using two energies from one of the sources and velocity is determined by comparison of the dynamic radiation signals received by the two detectors spaced axially along the pipe. This arrangement uses the minimum number of components and is thus particularly simple and cost advantageous.

One embodiment of the invention will now be described by way of example and with reference to the accompanying drawing, which is a side elevation in partial cross-section of the apparatus of the embodiment.

The apparatus 10 comprises two gamma radiation units 12,14, two pressure transducers 16,18 and a central processing unit 20.

The pressure transducers 16,18 are provided on either side of a static flow mixer 22 within the pipe 24. The pressure transducers 16,18 are connected to the central processing unit 20. Downstream of the mixer 22 is provided a temperature sensor 26 which is also connected to the central processing unit 20. Just downstream of the temperature sensor 26 is provided the first gamma radiation unit 12. The first gamma radiation unit 12 comprises a caesium source of energies 32 keV and 661 keV. The source directs its radiation through the pipe 24 to a single detector to the other side of the pipe 24. The detector is connected to an amplifier and analyzer 28 which has high and low outputs to the central processing unit 20. The amplifier and channel analyzer 28 is powered by a DC power supply 30 adjacent the central processing unit 20. Downstream of the first radiation unit 12 is provided the second radiation unit 14. This includes a single 661 keV caesium source and a thick crystal detector which is connected to a second amplifier and analyzer 32 which is also powered by the power supply 30 and is also connected to the central processing unit 20.

In use, a three phase fluid flow of oil, water and gas flows through the pipe 24 and through the mixer 22. The temperature sensor 26 senses its temperature and the pressure transducers 16,18 upstream and downstream of the mixer 22 provide pressure information to the central processing unit 20 to enable the pressure drop across the mixer 22 to be determined. High and low energy radiation from the source of the first radiation unit 12 is detected by the single detector of the first radiation unit 12 after absorption through the fluid and is processed and analyzed by the central processing unit 20 together with the signals from the second radiation unit 14. The signals from the first radiation unit 12 are chronologically divided and grouped into bands by magnitude for statistical analysis by the central processing unit 20 (which constitutes the aforesaid "processing means" and "analyzing means") to enable an accurate determination of phase fraction to be made. Second radiation unit 14 in combination with the signal from the first radiation unit 12 enables velocity to be calculated and this information together with the calculation of pressure drop enables the total and phase flow rates to be determined. The temperature sensor information is needed to take account of the fact that the gas constitutes a compressible phase.

Alternatively, or in addition, velocity may be derived from pressure drop across the mixer such that the second radiation unit 14 may be omitted.

The first radiation unit 12 may include two distinct caesium sources, or a single caesium source capable of radiating at both energies. Clearly, other types of radiation source may be used.

In a further embodiment, the first radiation unit 12 and second radiation unit 14 use different energies and source of only a single energy is provided in the first radiation unit.

We claim:

1. Apparatus for analysing fluid flow in a pipe comprising at least one radiation source to direct radiation through the flow, and at least one radiation detector positioned to receive from the source or sources radiation which has passed through the flow, the source or sources emitting radiation at least at two different energies, the or each detector providing a signal to processing means, the processing means being arranged to process the signal to provide a series of chronological values and to group the values by magnitude for analysis by analysis means.

2. Apparatus as claimed in claim 1, wherein the analysis means is arranged to determine the phase fractions in the flow.

3. Apparatus as claimed in claim 1 or claim 2, wherein the analysis means is arranged to determine the type of flow.

4. Apparatus as claimed in claim 1, wherein radiation from the or each source will be measured over a series of short time intervals.

5. Apparatus as claimed in claim 1, wherein a single source is provided.

6. Apparatus as claimed in claim 5, wherein the source is a caesium source.

7. Apparatus as claimed in any preceding claim, wherein the apparatus includes a mixer and means for sensing pressure drop across the mixer.

8. Apparatus as claimed in claim 7, wherein the apparatus includes means for sensing liquid hold-up.

9. Apparatus as claimed in claim 8, wherein the sensing means are associated with the analysis means which is arranged to determine flow rate.

10. Apparatus as claimed in claim 8, wherein the means for sensing the liquid hold-up comprises at least one radiation source to direct radiation through the flow to at least one radiation detector positioned to receive radiation which as passed through the flow from the or each source.

11. Apparatus as claimed in claim 10, wherein the apparatus includes only two sources and only two detectors and the analysis means is arranged to determine both phase fraction and flow rate.

12. Apparatus as claimed in claim 2, wherein radiation from the or each source will be measured over a series of short intervals.

13. Apparatus as claimed in claim 3, wherein radiation from the or each source will be measured over a series of short intervals.

14. Apparatus as claimed in claim 2, wherein a single source is provided.

15. Apparatus as claimed in claim 3, wherein a single source is provided.

16. Apparatus as claimed in claim 4, wherein a single source is provided.

17. Apparatus as claimed in claim 9, wherein the means for sensing the liquid hold-up comprises at least one radiation source to direct radiation through the flow to at least one radiation detector positioned to receive radiation which has passed through the flow from the or each source.

18. Apparatus as claimed in claim 17, wherein the apparatus includes only two sources and only two detectors and the analysis means is arranged to determine both phase fraction and flow rate.

* * * * *